US011413096B2

(12) United States Patent
Krüger

(10) Patent No.: US 11,413,096 B2
(45) Date of Patent: Aug. 16, 2022

(54) SYSTEM FOR THE RECONSTRUCTION OF SYMMETRICAL BODY PARTS

(71) Applicant: Intersect ENT GmbH, Hennigsdorf (DE)

(72) Inventor: Timo Krüger, Berlin (DE)

(73) Assignee: Intersect ENT GmbH, Hennigsdorf (DE)

( * ) Notice: Subject to any disclaimer, the term of this patent is extended or adjusted under 35 U.S.C. 154(b) by 209 days.

(21) Appl. No.: 16/668,445

(22) Filed: Oct. 30, 2019

(65) Prior Publication Data

US 2020/0069378 A1 Mar. 5, 2020

Related U.S. Application Data

(62) Division of application No. 14/909,627, filed as application No. PCT/EP2014/066754 on Aug. 4, 2014, now abandoned.

(51) Int. Cl.
*A61B 34/20* (2016.01)
*A61B 34/10* (2016.01)
(Continued)

(52) U.S. Cl.
CPC .............. *A61B 34/20* (2016.02); *A61B 34/10* (2016.02); *A61M 25/1018* (2013.01);
(Continued)

(58) Field of Classification Search
CPC ...... A61B 2034/108; A61B 2034/2068; A61B 34/10; A61B 34/20; A61M 25/1018;
(Continued)

(56) References Cited

U.S. PATENT DOCUMENTS

2006/0241388 A1 10/2006 Lavallee
2008/0319448 A1 12/2008 Lavallee et al.
(Continued)

FOREIGN PATENT DOCUMENTS

CN 101954146 A 1/2011
CN 202069641 U 12/2011
(Continued)

OTHER PUBLICATIONS

International Search Report and Written Opinion from PCT/EP2014/066754, dated Oct. 31, 2014.
(Continued)

*Primary Examiner* — Mark D Remaly
(74) *Attorney, Agent, or Firm* — Cooley LLP

(57) ABSTRACT

A medical system for assisting in the planning and/or performance of the reconstruction of normally symmetrical body parts of a patient comprises a measuring unit for measuring a first surface and a second surface for determining a topography of the first and second surfaces, a storage unit for storing the determined topographies of the first and second surfaces, an evaluation unit for establishing a mirror image of the stored topography of the first surface and for calculating deviations of the stored topography of the second surface from the first surface mirror image, and a control unit for outputting guidance information for at least one medical instrument on the basis of the calculated deviations of the topography of the second surface, in order to reconstruct the topography of the second surface according to the mirror image of the topography of the first surface.

16 Claims, 2 Drawing Sheets

(51) Int. Cl.
    *A61M 25/10* (2013.01)
    *G06T 7/00* (2017.01)
    *G06T 11/00* (2006.01)
    *G02B 26/10* (2006.01)

(52) U.S. Cl.
    CPC .......... *G06T 7/0016* (2013.01); *G06T 11/006* (2013.01); *A61B 2034/108* (2016.02); *A61B 2034/2068* (2016.02); *A61M 25/10188* (2013.11); *G02B 26/10* (2013.01); *G06T 2207/30004* (2013.01)

(58) Field of Classification Search
    CPC ............. A61M 25/10188; G02B 26/10; G06T 11/006; G06T 2207/30004; G06T 7/0016
    See application file for complete search history.

(56) References Cited

U.S. PATENT DOCUMENTS

2010/0113939 A1    5/2010    Mashimo et al.
2012/0016269 A1    1/2012    Moctezuma de la Barrera

FOREIGN PATENT DOCUMENTS

| | | |
|---|---|---|
| CN | 103127602 A | 6/2013 |
| DE | 10 2005 052 993 A1 | 5/2007 |
| EP | 0 097 001 A1 | 12/1983 |
| WO | 01/35842 A1 | 5/2001 |
| WO | 2004/110309 A2 | 12/2004 |

OTHER PUBLICATIONS

Office Action from Chinese Patent Application CN 201480049701.2, dated Sep. 4, 2017.

Office Action from German Patent Application DE 10 2013 215 395.3, dated Mar. 18, 2014.

SYSTEM FOR THE RECONSTRUCTION OF SYMMETRICAL BODY PARTS

CROSS REFERENCE TO RELATED APPLICATIONS

This application is a divisional application of U.S. application Ser. No. 14/909,627 filed Feb. 2, 2016, which is the U.S. National Stage of International Application Number PCT/EP2014/066754 filed on Aug. 4, 2014 which application claims priority under 35 USC § 119 to German Patent Application No. 10 2013 215 395.3 filed on Aug. 5, 2013. Each of the aforementioned applications are hereby incorporated by reference in their entirety.

TECHNICAL FIELD

The invention relates to a system for assisting in planning and/or performing the reconstruction of usually symmetrical body parts of a patient.

BACKGROUND OF THE INVENTION

In invasive surgical interventions, surgical instruments are moved in an operating region in the body of a patient by a surgeon during an operation. An operating region refers to the space in the interior of the patient which is potentially or effectively affected by the employed surgical instruments during the operation. The operation includes the insertion and removal of surgical instruments into the body of the patient and out of the body of the patient, as well as the movement of the surgical instruments within the body of the patient and the use of the surgical instruments in an intervention region which is arranged in the operating region and precisely predefined. The intervention region refers to the part in the operating region which is to be worked on by the surgeon. By way of example, this can relate to the tissue to be removed or vessels to be closed. Accordingly, an operating region may comprise a plurality of intervention regions. A multiplicity of sensitive structures lie next to the intervention regions in the operating region and they are to be preserved from damage by the surgical instruments. The sensitive structures include, for example, vessels, organs, nerves, muscles, ligaments, sinews and other, generally intact tissue which is intended to be maintained in order to restrict the effects of the operation to a necessary minimum, as any further impairment of the body of the patient during the operation may increase the health risk to the patient and have a negative influence on the result of the operation.

Tumor diseases, accidents or defects present at birth often require reconstruction of the tissue of the patient. In so doing, functional and aesthetic aspects are to be taken into account when rebuilding the bone and soft tissue structure of the patient, particularly in the facial region. In the case of such interventions in the face of the patient, it is particularly important for the face to have symmetry that is as exact as possible after the operation, as even slight deviations from the symmetry are already clearly perceivable and may constitute a permanent functional and also psychological burden for the patient.

When planning the rebuilding or reconstruction of the bone and soft tissue structure of the face of the patient, the plane of symmetry of the face is usually established first. To this end, the geometric situation of the face is detected by means of optical methods, e.g. on the basis of pattern projection or a laser distance measurement. Using various methods, the plane of symmetry can be determined automatically from the surface structure of the face established therewith. In a subsequent step, the surface structures of the two sides separated by the plane of symmetry are established, compared to one another and hence differences are established. This is generally carried out by means of complicated CAD programs, which are only designed for particularly highly trained users.

Moreover, systems for the navigation on the basis of the bone structures are known and used, e.g. in the case of surgical interventions on the spinal column or in the field of ENT. Such systems generally comprise a position detection system for detecting the positions of medical instruments and of the patient in a reference coordinate system and a guidance system for provision of guidance data for navigating the surgical instruments. By coordinating the guidance of the medical instruments, conventional navigation systems significantly unburden the surgeon, as this object requires a large degree of spatial imagination. Accordingly, the risk of the operation is lowered and the results of the operation are improved.

In known navigation or position detection systems, the instrument or patient position is usually determined on the basis of optical or electromagnetic methods, with systems with optical methods being more common. In conventional electromagnetic methods, the position of the medical instruments is measured in an alternating electromagnetic field generated by a field generator by way of the strength of currents which are induced in a position sensor that is arranged at the medical instrument. It is well known that position sensors suitable herefor have a plurality of coils, in particular three coils. However, electromagnetic position detection systems are disadvantageous in that possible error sources, such as e.g. active surgical instruments which likewise emit an electromagnetic field during operation, need to be detected and compensated for.

Known measuring and navigation systems are all disadvantageous in that they cause relatively high procurement costs, often have great complexity and can only be operated by specifically trained specialists. Furthermore, these systems are often cumbersome in terms of handling and therefore provide a multiplicity of potential error sources. Moreover, these systems all require image data of the patient and therefore need a long preparation time and may, in certain circumstances, lead to additional radiation exposure of the patient.

SUMMARY OF THE INVENTION

Therefore, it is the object of the present invention to provide a method and a system for planning and performing the navigation when rebuilding symmetrical body parts of the patient, which do not have the aforementioned disadvantages.

According to the invention, this object is achieved by a medical system for assisting in planning and/or performing the reconstruction of usually symmetrical body parts. The system comprises at least one measuring unit for measuring a first area and a second area in order to establish a topography of the first area and the second area. This can relate to areas or surfaces of a patient, wherein the areas are selected to satisfy the criterion that the first area in a healthy human is usually substantially mirror symmetrical in relation to the second area. Furthermore, provision is made of a storage unit for storing the established topographies of the first area and the second area of the patient. The system moreover has an evaluation unit for establishing a mirror image of the stored topography of the first area and for calculating deviations between the stored topography of the second area and the mirror image of the stored topography of the first area, as well as a control unit for outputting guidance information for at least one medical instrument on the basis of the calculated deviations in the topography of the second area from the mirror image of the stored topography of the first area in order to reconstruct the topography of the second area in accordance with the mirror image of the topography of the first area. Using a system according to the invention, a topography of two symmetry halves of usually symmetrical body parts is establishable. If a symmetry half to be treated has an ACTUAL topography which has asymmetries in relation to the corresponding intact symmetry half, an INTENDED topography can be established by mirroring the topography of the corresponding intact symmetry half for the purposes of producing or reconstructing the symmetry of the symmetry half to be treated. Guidance information for controlling at least one medical instrument is generable from the deviations between the ACTUAL topography and the INTENDED topography.

Preferably, the medical system has a data transmission interface for transmitting the topography data of a surface established by the measuring unit to the evaluation unit and/or storage unit. In this case, the measuring unit can be connected by cables or comprise a radio device for transmitting the measured values.

In a first embodiment of the invention, at least one measuring unit comprises a mechanical sensing device for mechanically sensing an area. By way of example, the sensing device can comprise a pointer with an instrument handle and an instrument tip for sensing the area or individual measurement points. The sensing device can be integrated in a position detection system such that position data from a sensing tip of the sensing device are establishable by the position detection system and displayable on a display unit. Using such a sensing device, the position of individual measurement points of an area is detectable in the coordinate system of the position detection system and hence the topography of the area is establishable by mechanical sensing.

Particularly preferably, the mechanical sensing device comprises a pointer with an at least partly spherically shaped instrument tip. Such instrument tips are advantageous in that they can be guided well over an area of the patient in a sliding manner, without injuring the area. Alternatively, pointers with a pointed or conical instrument tip are usable, particularly for sensing individual measurement points, since a point can be actuated more precisely using such an instrument tip.

In a second embodiment of the invention, at least one measuring unit comprises an optical sensing device for optically sensing an area. In the process, light waves are emitted and reflections and/or shadow formations are detected using optical means. Conclusions about the embodiment of the topography of the respective area can be drawn from the results.

Preferably, the optical sensing device comprises a laser and/or a video device and/or a photocell. Particularly preferably, the image data established by the optical sensing device are displayable on a display unit such as e.g. a monitor.

Particularly preferably, the system is embodied to automatically identify natural symmetries on the basis of recordings, e.g. photos. To this end, the system can have a detection unit, for example an optical reading unit, which can acquire a recording which comprises both the first area and the second area to be reconstructed. The system can establish INTENDED lines of symmetry from the acquired recording and, in a second step, preferably also establish the deviation of the ACTUAL topography of the second area from the INTENDED topography—the mirror image of the first area—thereof. To this end, use is preferably made of stereoscopic recordings, 3D recordings or else of models produced by tomography.

The evaluation unit can be embodied to take into account possible swellings of tissue in the tissue situated in the region of the second area when calculating deviations between the stored topography of the second area and the mirror image of the stored topography of the first area. What can be achieved thereby is that, post surgery, a second area to be reconstructed has a desired topography after detumescence of the tissue situated in the region of the second area. Swelling of the tissue can, for example, be taken into account by a supplemental value added to a sensed value established by optical or mechanical means. The supplemental value can be formed by a height difference between the swollen and detumescent state of the tissue. By way of example, a detumescent state can be predicated by a tissue model which can be stored in the evaluation unit. By way of example, the tissue model can include a skin tension characteristic, which is preferably established by optical and/or mechanical means. More preferably, the system is embodied to measure the topography of naturally symmetrical cavities, wherein a first cavity comprises the first area and a second cavity comprises the second area.

Alternatively or additionally, the evaluation unit can be embodied to necessarily include points of the topography of the second area defined as intact when producing the mirror image of the stored topography of the first area. By way of example, junctions of a bone, particularly one situated in, or in the vicinity of, the region to be reconstructed, can be defined as intact points. As a result, the mirror image of the stored topography of the first area can thus be deformed imperfectly, i.e. it can be asymmetrical in relation to the topography of the first area, particularly in the region of the junction of a bone. Thus, by way of example, in the case of a left upper jaw half to be reconstructed (in which the second area lies) on the basis of a right upper jaw half (in which the first area lies) with an axis of symmetry situated in the anterior apposition surface, the left cheekbone can be defined as an intact junction. Since the human face is typically slightly asymmetrical, an offset would emerge between the left upper jaw half and the left cheekbone in the case of perfect mirroring of the right upper jaw half about the axis of symmetry situated in the anterior apposition surface. By defining the left cheek bone as an intact junction, this junction is now included by the evaluation unit when producing the mirror image of the stored topography of the first area. The mirror image of the stored topography of the first area is now distorted in the region of this junction such that the left upper jaw half can be reconstructed without offset in relation to the left cheekbone.

In an advantageous embodiment of the invention, at least one medical instrument is embodied as a balloon catheter. In accordance with the guidance information output by the control unit, the balloon catheter is fillable with a work fluid. The process of filling the balloon catheter is preferably controllable automatically by the medical system, and so a manual intervention by the surgeon is substantially only necessary in emergencies. To this end, the medical system particularly preferably has a connector for the work fluid or a corresponding pressure generator, such as e.g. a compressor.

Preferably, the system has at least one sensor for detecting the internal pressure and/or the extent of the balloon catheter. Conventional pressure sensors for fluids are suitable as a sensor for establishing the internal pressure of the balloon catheter. By way of example, measuring the extent of the balloon catheter can be carried out by way of strain gauges. A plurality of strain gauges, each arranged in the direction of one of the strain components to be determined, are provided for establishing the multi-axis extent of the balloon catheter. Particularly preferably, at least two strain gauges have an angle of 90° in relation to one another.

It is furthermore preferable for the data acquired by the sensor to be transmittable to the control unit by way of a sensor data interface.

More preferably, the control unit is embodied to control the filling of the balloon catheter taking into account the data established by the sensor. Hence, the control unit can terminate the filling of the balloon catheter once the balloon catheter has a desired extent.

Preferably, the control unit is embodied to control a filling speed of the balloon catheter in a manner dependent on the respective extent and/or on the internal pressure of the balloon catheter, wherein the filling speed is tendentiously intended to decrease with increasing extent or with increasing internal pressure of the balloon catheter. Hence, a load on, and possible damage to, the tissue to be produced or to be reconstructed can be reduced.

In an advantageous embodiment of the invention, the balloon catheter has a plurality of chambers, wherein the chambers are fillable independently of one another.

As a result of this, geometries that are more complicated can be obtained using a balloon catheter since the individual chambers are fillable to a different extent, according to requirements.

Preferably, the evaluation unit is configured to establish deviations in the topography of the second area from the mirrored topography of the first area on the basis of individual representative measurement points on the second area. Accordingly, there is no need to measure a multiplicity of measurement points which are arranged between two representative measurement points or the position of which need not be changed within the scope of the production or reconstruction. As a result, the number of measurement points to be sensed in the second area is significantly reducible. As a result of this, there is also significant reduction in the impairment or risk of injury to the patient and in the work complexity during sensing.

Particularly preferably, the measuring unit is embodied to establish the topography of the second area, at least at representative measurement points, during the production or reconstruction of the second area. Hence, the progress of the intervention can be established during the process of producing or reconstructing the second area.

More preferably, the control unit adapts the guidance information for at least one medical instrument on the basis of the topography data of the second area established during the reconstruction of the second area. In the case of unpredictable deviations in the topography of the second area from corresponding intended values, the expansion of the balloon catheter, for example, can be automatically stopped by the control unit in order to prevent injury to the patient.

In an advantageous embodiment of the invention, the medical instrument is an active medical instrument, wherein the control unit is embodied to control the operating state of the active medical instrument in a manner dependent on the position of the active medical instrument from the topography of the second area established by the control unit.

Therefore it is possible to stop, i.e., for example, switch off, an active medical instrument, e.g. a cutting instrument, when the instrument tip is arranged at a point in the established topography of the second area at which no cut is intended to be carried out. Accordingly, the active medical instrument can be put into the active operating state, or remain therein, when the instrument tip is arranged at a point in the established topography of the second area, at which a cut is intended to be performed. Provision can likewise be made for turning down the active medical instrument when it approaches a point at which no cut is intended to be performed and for increasing the operating state of the active medical instrument when it moves away from such a point.

BRIEF DESCRIPTION OF THE DRAWINGS

Below, the invention is intended to be explained in more detail on the basis of an exemplary embodiment, with reference being made to a drawing. Herein.

DETAILED DESCRIPTION

Figure 1:
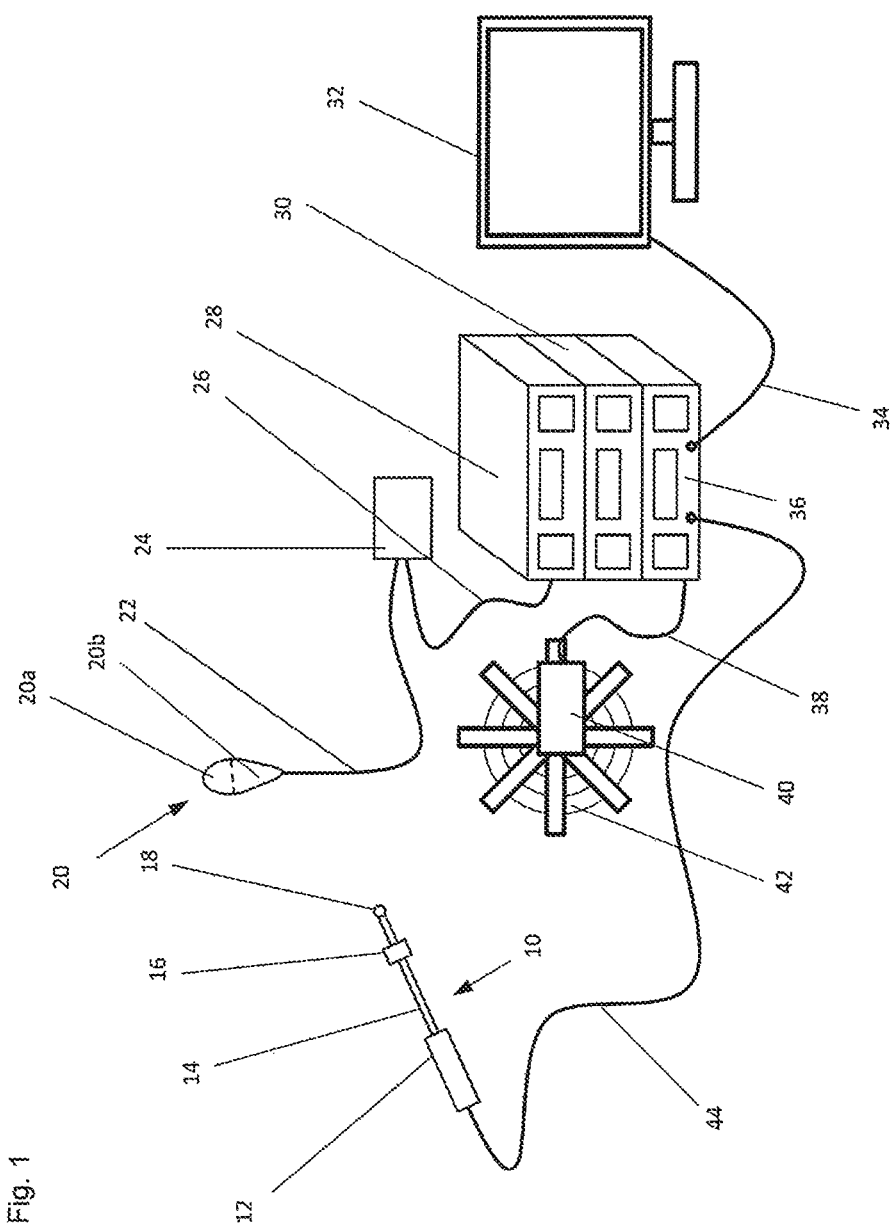
FIG. 1 shows an embodiment of a medical system for assisting in planning and/or performing the reconstruction of usually symmetrical body parts of a patient.

The exemplary embodiment of a medical system according to the invention imaged in FIG. 1 comprises an evaluation unit 36, a storage unit 30, a control unit 28, a pointer 10, a field generator 40, a balloon catheter 20 with a fluid compressor 24, and a display unit 32.

The pointer 10 is connected to the evaluation unit 36 by way of an instrument cable 44 and has a proximal instrument handle 12, a spherical instrument tip 18, an instrument shaft 14 arranged coaxially with the instrument handle 12 between the instrument handle 12 and the instrument tip 18, as well as an instrument sensor 16, which is arranged at the instrument shaft 14 in this embodiment. Alternatively, the instrument sensor 16 can also be arranged at the instrument tip 18. As an alternative to the spherical form, the instrument tip 18 can, for example, also have a conical, tetrahedral or pyramid shape, with the pointed part preferably pointing in the distal direction. Using the instrument tip 18, it is possible to sense an area of a patient, registered in the position detection system, in a line-shaped or point-shaped manner. Prior to this, the patient needs to be registered in the position detection system so that the position of the patient is known in the coordinate system of the position detection system. To this end, a patient localizer (not depicted here) is arranged in an immovable manner on the patient, with currents being induced in the patient localizer in a manner dependent on the position of the patient localizer in respect of the field generator 40. These currents are measurable by the evaluation unit 36. The patient is registrable in the position detection system by way of a sensing process of individual representative points on the body of the patient using the pointer 10.

During the sensing procedure of the area of the patient registered in the position detection system, the pointer 10 is guided either in a manner sliding over the area or directly to individual measurement points. The measurement points are preferably to be selected in such a way that they represent specific points in the area, e.g. protruding bones. In the case of sliding guidance, the position data of the instrument tip 18 can be detected continuously by the evaluation unit 36 and stored in the storage unit 30. In the case of direct actuation of individual measurement points, at least the location of the instrument tip 18 when reaching the measurement point is to be detected and stored. By way of appropriate software, areas lying between two points can be reconstructed by calculation. In this manner, a topography of the sensed area of the patient is establishable and storable.

The location of the instrument tip 18 is determined by way of a position detection system integrated into the evaluation unit 36. The field generator 40 is connected by way of a generator cable 38 to the evaluation unit 36 and controlled by the latter. The field generator 40 emits an alternating electromagnetic field 42 which, in a manner dependent on the location of the instrument sensor 16 relative to the field generator 40, induces currents in the instrument sensor 16. Preferably, the instrument sensor 16 has three coils, and so three currents are induced. The current strengths are measured by the evaluation unit 36 and hence the position of the instrument sensor 16 is determined relative to the field generator 40. If the pointer 10 was previously registered in the position detection system, the position of the instrument tip 18 is also known thus.

The evaluation unit 36 may have software, by means of which symmetrical areas are identifiable and axes of symmetry are establishable. Alternatively, the axes of symmetry can also be defined manually, for example by way of appropriate marking of points lying on an axis of symmetry with the aid of the pointer 10. The evaluation unit 36 is configured to mirror the topography of a first area, which is referred to as reference area, by way of the axis of symmetry and to compare the mirror image of the topography of the first area with the topography of a second area, with the topography of the second area ideally already corresponding to the topography of the mirrored first area in respect of position and form. To the extent that the topography of the second area deviates from the mirror image of the topography of the first area, the evaluation unit 36 can establish the difference between the two areas and, from this, determine a correction value which can be forwarded to the control unit 28. On the basis of the correction value, the control unit 28 can control the filling of the balloon catheter 20 by means of the fluid compressor 24 and a catheter tube 22, which connects the fluid compressor 24 to the balloon catheter 20. The fluid compressor 24 is connected to the control unit 28 by way of a compressor cable 26.

Various image data of the patient, medical instruments and prostheses are displayable on the display 32, which is connected to the evaluation unit 36 by way of a display cable 34. Said image data can refer to the image data obtained both prior to surgery and also during surgery, which image data are imageable separately next to one another on virtual screens or in a superposed manner on one screen. Particularly in the case of the superposed representation, it is important that all superposed objects are registered in the position detection system such that position and location of the individual objects can be assigned to the reference coordinate system of the position detection system. In this example, the display 32 is a monitor.

Figure 2:
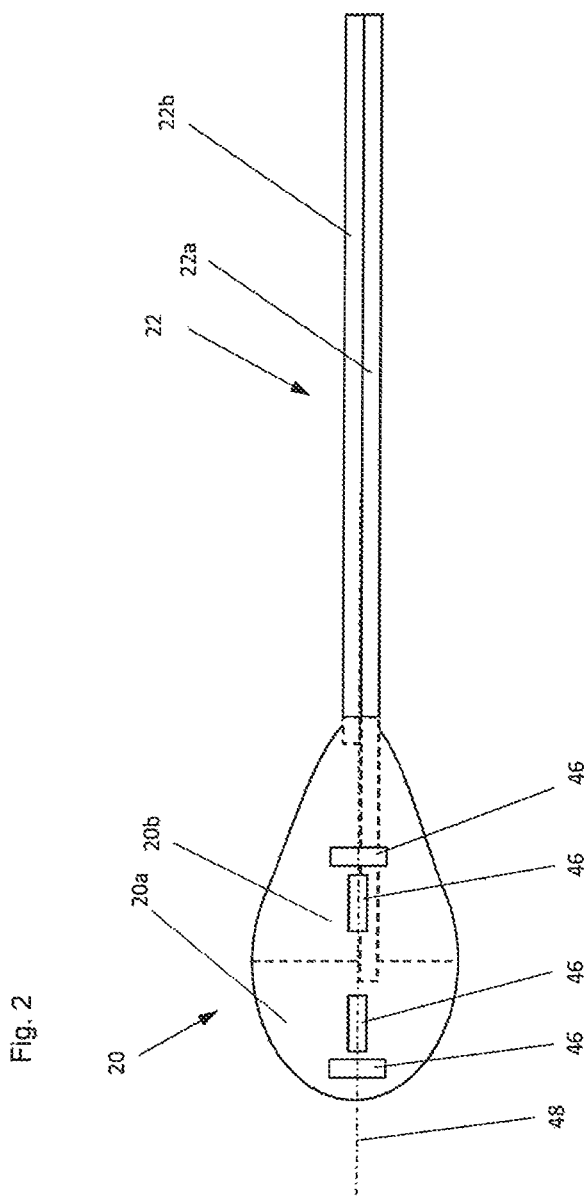
FIG. 2 shows a magnified side view of a balloon catheter from FIG. 1 with two pressure chambers.

The balloon catheter 20 from FIG. 1 is imaged in a magnified side view in FIG. 2 and it has a first chamber 20a and a second chamber 20b, wherein the first chamber 20a and the second chamber 20b are fillable separately from one another by way of a first channel 22a and a second channel 22b, respectively, of the catheter tube. Strain gauges 46 are arranged on the balloon catheter 20 in a manner distributed along the outer circumference, wherein some strain gauges 46 are aligned parallel to and some strain gauges 46 are aligned across the longitudinal axis 48 of the balloon catheter 20. The expansion of the balloon catheter 20 as a result of the filling is determinable by way of the strain gauges 46. The strain gauges are connected to the evaluation unit 36 and/or the control unit 28 by way of a cable (not depicted here) such that the evaluation unit 36 or the control unit 28 can determine the expansion of the balloon catheter 20 on account of the modified resistances of the strain gauges 46. If the expansion reaches a threshold, the control unit 28 can reduce or stop the filling of the balloon catheter 20 or of the first chamber 20a or the second chamber 20b of the balloon catheter 20.

The balloon catheter 20 shown in FIG. 2 has an egg-shaped form with two chambers separated from one another. Alternative embodiments may comprise a multiplicity of further chambers, which are preferably fillable separately from one another by way of an appropriate catheter tube 22. Depending on application, the outer form of the balloon catheter 20 can also have a cylindrical or substantially planar embodiment. In addition or as an alternative to the use of strain gauges 46, the balloon catheter 20 can have pressure sensors (not shown in the drawings), which are arranged in the first chamber 20a and/or in the second chamber 20b in order to detect the respective chamber internal pressure. In a manner analogous to the strain gauges 46, the expansion of the balloon catheter 20 is automatically determinable by the evaluation unit 36 by way of the chamber internal pressure established by the pressure sensors in conjunction with information about the expansion properties of the balloon catheter 20 and hence the filling process can be subject to closed-loop control.

LIST OF REFERENCE SIGNS

10 Pointer
12 Instrument handle
14 Instrument shaft
16 Instrument sensor
18 Instrument tip
20 Balloon catheter
20a First chamber
20b Second chamber
22 Catheter tube
22a First channel
22b Second channel
24 Fluid compressor
26 Compressor cable
28 Control unit
30 Storage unit
32 Display unit
34 Display cable
36 Evaluation unit
38 Generator cable
40 Field generator
42 Electromagnetic field
44 Instrument cable
46 Strain gauges
48 Longitudinal axis

The invention claimed is:

1. A method for assisting in planning or performing reconstruction of usually symmetrical body parts of a patient, comprising:
measuring a first area and a second area in order to establish a topography of the first area and the second area;
storing topography data of the established topographies of the first area and the second area;

establishing a mirror image of the stored topography of the first area;

calculating deviations between the stored topography of the second area and the mirror image of the stored topography of the first area;

automatically generating guidance information for at least one medical instrument on the basis of said deviations;

outputting the generated guidance information to the at least one medical instrument;

controlling the at least one medical instrument in accordance with the guidance information in order to reconstruct the topography of the second area in accordance with the mirror image of the topography of the first area;

establishing the topography of the second area, at least at representative measurement points, during the reconstruction of the second area; and adapting the guidance information for the at least one medical instrument on the basis of said topography data of the second area established during the reconstruction of the second area.

2. The method as claimed in claim 1, wherein the at least one medical instrument is a balloon catheter which, in accordance with the guidance information, is fillable with a work fluid.

3. The method as claimed in claim 2, further comprising detecting by at least one sensor an internal pressure or extent of the balloon catheter; and controlling the filling of the balloon catheter taking into account the internal pressure or extent of the balloon catheter established by the sensor.

4. The method as claimed in claim 1, wherein calculating deviations in the topography of the second area from the mirrored topography of the first area is on the basis of individual representative measurement points on the second area.

5. The method as claimed in claim 1, wherein the at least one medical instrument is an active medical instrument, and the method further comprises controlling the operating state of the active medical instrument in a manner dependent on the position of the active medical instrument from the established topography of the second area.

6. The method as claimed in claim 2, wherein the balloon catheter comprises a plurality of chambers that are independently fillable with the work fluid.

7. The method as claimed in claim 3, wherein the at least one sensor comprises a first sensor aligned parallel to a longitudinal axis of the balloon catheter and a second sensor aligned across the longitudinal axis of the balloon catheter.

8. The method as claimed in claim 1, wherein measuring a first area and a second area is performed with a mechanical sensing device.

9. The method as claimed in claim 8, wherein the mechanical sensing device comprises a pointer with an instrument handle and an instrument tip for sensing.

10. The method as claimed in claim 1, wherein measuring a first area and a second area is performed with an optical sensing device.

11. The method as claimed in claim 10, wherein the optical sensing device comprises at least one of a laser, a video device, and a photocell.

12. The method as claimed in claim 1, wherein establishing a mirror image of the stored topography of the first area comprises automatically identifying a line of symmetry based on one or more images.

13. The method as claimed in claim 12, wherein the one or more images comprise a stereoscopic recording, a 3D recording, or a tomographic model.

14. The method as claimed in claim 1, further comprising defining one or more points in the second area as an intact point and deforming the mirror image of the stored topography of the first area based on the one or more intact points.

15. The method as claimed in claim 1, wherein calculating deviations between the stored topography of the second area and the mirror image of the stored topography of the first area comprises incorporating a supplemental value representing tissue swelling in the second area.

16. The method as claimed in claim 1, wherein generating guidance information for at least one medical instrument comprises determining a correction value based on the calculated deviations between the stored topography of the second area and the mirror image of the stored topography of the first area.

* * * * *